United States Patent [19]

Cohen

[11] Patent Number: 4,969,867
[45] Date of Patent: Nov. 13, 1990

[54] SLEEP-PROMOTING AND/OR PACIFICATION APPARATUS

[75] Inventor: Ruben Cohen, Kibbutz Mishmar Hanegev, Israel

[73] Assignee: Pama Electronics, Kibbutz Mishmar Hanegen, Israel

[21] Appl. No.: 229,954

[22] Filed: Aug. 9, 1988

[30] Foreign Application Priority Data

Aug. 14, 1987 [IL] Israel .................................... 83537

[51] Int. Cl.⁵ .................................... A61M 21/00
[52] U.S. Cl. .................................... 600/28
[58] Field of Search ..................... 600/26, 27, 28

[56] References Cited

U.S. PATENT DOCUMENTS

| | | | |
|---|---|---|---|
| 3,137,092 | 6/1964 | Salerno | 600/28 |
| 3,292,611 | 12/1966 | Belkin | 600/28 |
| 3,563,229 | 2/1971 | Petrussion | 600/28 |
| 3,672,354 | 6/1972 | Weber | 600/26 |
| 3,712,292 | 1/1973 | Zentmeyer, Jr. | 600/28 |
| 3,888,233 | 6/1975 | Ware | 600/28 |
| 3,994,282 | 11/1976 | Moulet | 600/28 |
| 4,124,022 | 11/1978 | Gross | 600/28 |
| 4,573,449 | 3/1986 | Warnke | 600/28 |
| 4,788,533 | 11/1988 | Mequignon | 600/28 |
| 4,819,616 | 4/1989 | Samson | 600/28 |

*Primary Examiner*—Kyle L. Howell
*Assistant Examiner*—Kevin Pontius
*Attorney, Agent, or Firm*—Benjamin J. Barish

[57] ABSTRACT

Apparatus for promoting sleep in an individual, comprises a blanket, mattress, pillow or similar article adapted to be placed against and/or around the individual; a plurality of compressional-wave transducers incorporated in the article at a plurality of locations for producing compressional waves; and an electrical circuit for generating electrical signals energizing the transducers to produce sleep-promoting compressional waves at the plurality of different locations.

20 Claims, 3 Drawing Sheets

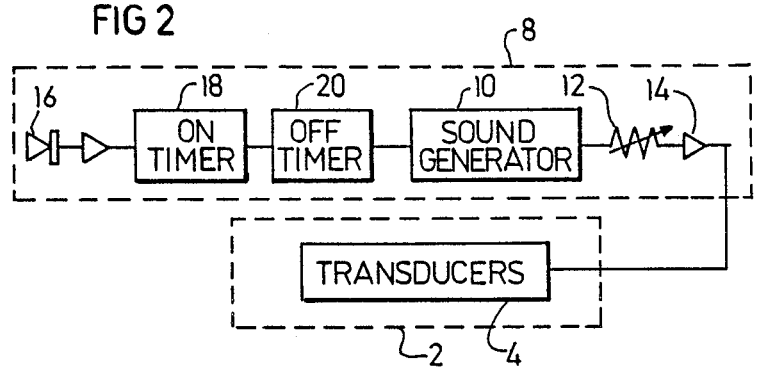
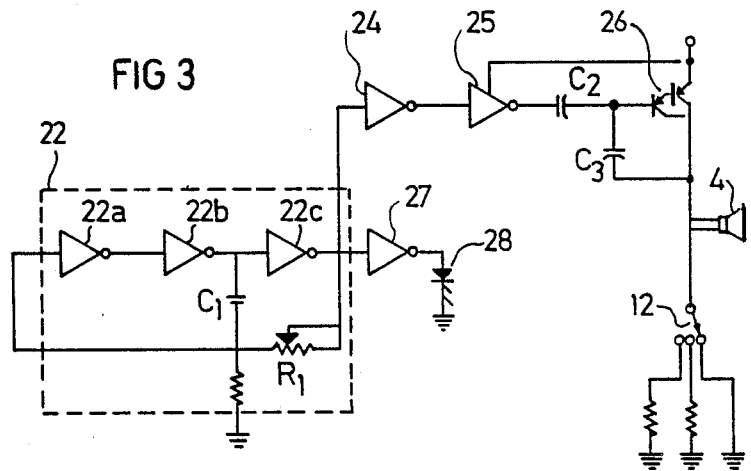
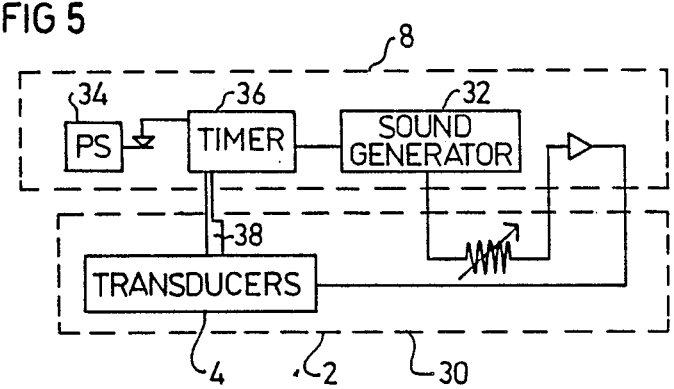

SLEEP-PROMOTING AND/OR PACIFICATION APPARATUS

BACKGROUND OF THE INVENTION

The present invention relates to sleep-promoting and/or pacification apparatus, and particularly to apparatus useful for promotion sleep and/or pacifying adults or infants.

A significant segment of the population suffers from insomnia, i.e., the chronic inability to fall asleep, usually due to some form of psychological restlessness in the individual. Restlessness in an infant is usually manifested by the infant crying, particularly before the infant falls asleep. When this occurs, the infant's mother, intuitively, may hold the infant in her arms against her body, which usually pacifies the infant. This phenomenon, which has been extensively investigated by pediatricians and scientists, is generally attributed to the fact that the infant, while in the mother's womb, is in a living, active environment involving movement and activity produced by the beating heart of the mother; and upon emerging to the external world, the new environment creates a feeling of uneasiness and insecurity. When the mother holds the infant against her body, usually intuitively on the left side, the womb environment is partially restored, decreasing this feeling of uneasiness and insecurity and thereby promoting sleep.

With respect to sleeplessness on the part of adults, it has been found that periodic monotonous sounds, such as produced by various home appliances as ventilators, air conditioners, and the like, frequently are effective in promoting sleep.

An object of the present invention is to provide apparatus particularly useful for promoting sleep and/or pacifying both infants and adults.

BRIEF SUMMARY OF THE INVENTION

According to the present invention, there is provided apparatus for promoting sleep in an individual, comprising: a blanket, mattress, pillow or similar article adapted to be placed against and/or around the individual; a plurality of compressional wave transducers incorporated in said article and distributed over a relatively large surface area at a plurality of different locations thereof for producing compressional waves at said plurality of locations; and an electrical circuit for generating electrical signals energizing said transducers to produce sleep-promoting compressional waves at said plurality of different locations.

The compressional-wave transducers may be sonic, supersonic or subsonic transducers, such as the constrictive or expansive type. As one example, there may be used small speakers which produce audible sounds.

In the preferred embodiments of the invention described below, the article is a blanket having inner and outer layers, and the plurality of transducers are sandwiched between the inner and outer layers. The electrical circuit, included in a separate unit, comprises a signal generator generating monotonous sounds in substantially one persistent tone.

Two embodiments of the invention are described below for purposes of example.

One described embodiment is particularly useful for promoting sleep in or pacifying an infant. In this embodiment, the signal generator generates an electric signal simulating the human heartbeat. This embodiment further includes a sound sensor for sensing the crying of the infant and effective in response thereto, to actuate the signal generator.

The second embodiment of the invention described is particularly useful for promoting sleep in an adult for pacifying an adult while subject to disturbing or psycopathological stresses. This embodiment includes a variable-frequency oscillator controlled by a programmable counter-timer programmed for the individual user for producing a sequence of pleasant tones at a predetermined pitch. This embodiment further includes preadjustable attenuator means for causing the periodic sounds to fade out at a preselected rate.

Further features of the invention will be apparent from the description below.

BRIEF DESCRIPTION OF THE DRAWINGS

The invention is herein described, by way of example only, with reference to the accompanying drawings, wherein:

FIG. illustrates one form of sleep-producing apparatus constructed in accordance with the present invention;

FIG. 2 is a block diagram illustrating one embodiment particularly useful for pacifying or promoting sleep in infants;

FIG. 3 more particularly illustrates the sound-generating circuit in FIG. 2;

FIG. 5 is a block diagram illustrating a second embodiment of the invention particularly useful for promoting sleep in adults.

DESCRIPTION OF PREFERRED EMBODIMENTS

Figure 1:
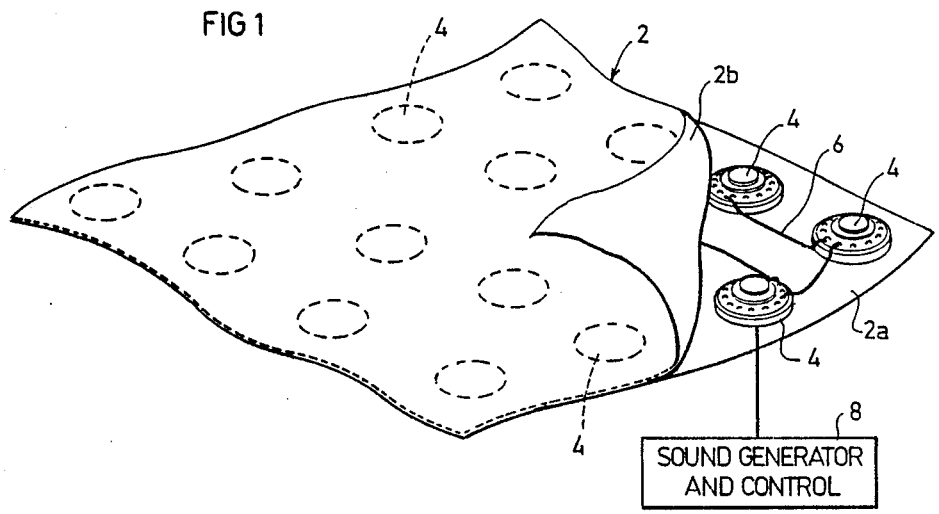

The sleep-promoting apparatus illustrated in FIG. 1 comprises a blanket, generally designated 2, made up of an inner layer 2a and an outer layer 2b. Sandwiched between the two layers 2a, 2b are a plurality of sound transducers 4 distributed uniformly at a plurality of different locations. In the example illustrated in FIG. 1, the sound transducers 4 are miniature speakers uniformly distributed within the blanket 2 according to a rectangular matrix. Preferably, the blanket includes at least nine of such sound transducers, 12 being shown in the example illustrated in FIG. 1. All are connected by electrical wiring, generally designated 6, to a sound or compressional-wave generator and control unit 8. Unit 8 includes an electrical circuit for generating the electrical signals which energize the transducers 4 and cause them to produce the sounds or compressional waves at the respective locations. Preferably, these sounds or compressional waves are hardly heard, but rather are sensed by the skin of the user, e.g., by the tender skin of an infant and by other physiological receptors distributed over the infant's body, promoting a sense of being in an active environment.

Figure 4:
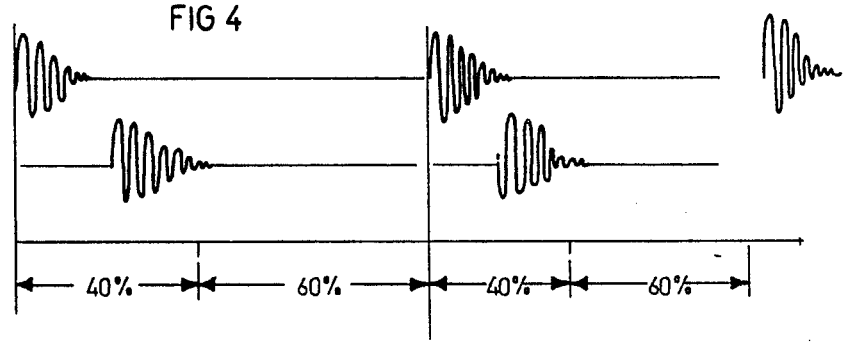
FIG. 4 illustrates waveforms produced by the apparatus of FIGS. 2 and 3.
Figure 6:
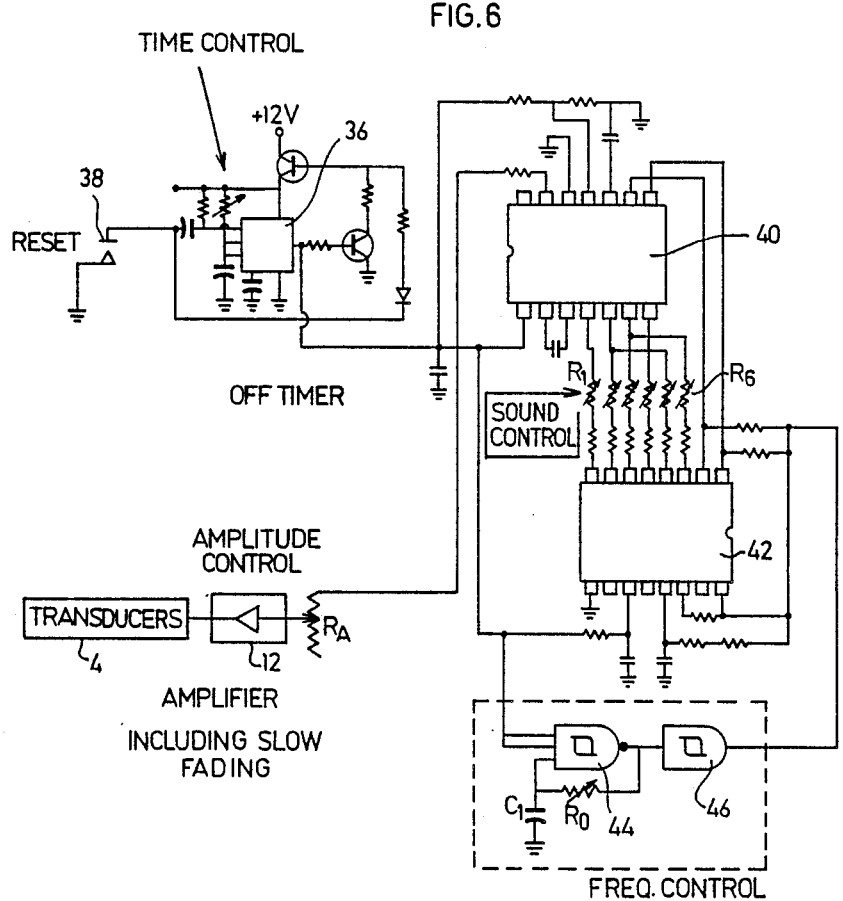
FIG. 6 illustrates an electrical circuit which may be used for implementing the block diagram of FIG. 5.

FIGS. 2–4 illustrate one embodiment of the invention particularly useful for pacifying or promoting sleep on the part of infants; and FIGS. 5 and 6 illustrate a second embodiment of the invention particularly useful for promoting sleep on the part of adults. Both embodiments use the blanket 2 (FIG. 1) for carrying the plurality of sound transducers 4, but it will be appreciated that in both embodiments, the transducers may be carried by another article, such as a mattress or pillow, or a combination of them, adapted to be placed against or around the individual such that the individual will hear or "feel" the sounds or other compressional waves outputted by the transducers.

Reference is first made to the FIGS. 2–4 embodiment for use with infants. In the block diagram illustrated in FIG. 2, the blanked (or mattress, or pillow, or combination of them) containing the transducers 4 is designated by block 2, and the elements of the sound generator and control unit are included within block 8. This control unit includes a sound generator 10 which generates the electrical signals applied, via a volume-control unit 12 and amplifier 14, to the transducers 4 for producing the sounds in the transducers. Sound generator 10 and volume-control unit 12 are described below particularly with reference to FIG. 3.

The sound generator and control unit 8 in FIG. 2 is equipped with means, in the form of a microphone 16, for sensing when the infant is crying, so that the system can, if desired, be automatically actuated whenever the infant cries for a predetermined time interval. For this purpose, the system further includes an On-timer 18 and an Off-timer 20. On-timer 18 enables the system to be preset to energize the sounds generator 10 and transducers 4 automatically after the infant has been crying for a predetermined time interval; and Off-timer 20 may be preset to fix the time interval in which the system operates after having been turned on, either automatically by the On-timer 18, or manually by a manual button (not shown).

FIG. 3 illustrates an electrical circuit which may be used for the sound generator 10 and volume control unit 12 of FIG. 2. The circuit illustrated in FIG. 3 includes a square-wave oscillator 22, comprising three amplifiers 22a, 22b, 22c, whose frequency of oscillation is determined by capacitor $C_1$ and variable resistor $R_1$. Resistor $R_1$ converts the oscillator from a 50—50 duty cycle to a 60—60 duty cycle, as described below with respect to FIG. 4.

The square-wave output of oscillator 22 is amplified in amplifiers 24, 25, and is then converted, by a Darlington switch 26 and a capacitor $C_3$, to decreasing sinusoidal waves as illustrated in FIG. 4, simulating the sounds of the human heartbeat. These signals are fed through sound transducers 4 via volume-control selector switch 12, corresponding to volume-control 12 in FIG. 2.

FIG. 4 illustrates the signal waveforms inputted into the sound transducers 4. It will be seen that there are two such waveforms for each heartbeat, one representing the sounds produced by the heart during systole, and the other representing the sounds produced by the heart during diastole. Both the systole and diastole sounds occupy 40% of each period, thereby producing a 40-60 duty cycle rather a 50—50 duty cycle; a 40-60 duty cycle more closely simulates the actual heartbeat sounds. As indicated above, resistor $R_1$ in FIG. 3 converts the oscillator to a 60:40 duty cycle. The heartbeat rate should be adjustable within a range of 40 to 120, i.e., 80 ±5%, heartbeats per minute.

The circuit in FIG. 3 further includes a light indicator 28, preferably a green LED (Light Emitting Diode), which is energized from the oscillator 22 via driver 27. LED 28 is preferably green with a gray diffusing cover for softening purposes since this has been found to have a relaxing or semi-hypnotic effect, which further contributes to the promotion of sleep when the illustrated apparatus is used.

The system illustrated in FIGS. 5 and 6 is particularly useful for adjust. The blanket (or mattress or pillow or combination of them), including the transducers 4, is schematically illustrated by block 2, and the sound generator and control unit is schematically illustrated by block 8, corresponding to the same numbered elements in FIG. 1. In FIG. 5, however, the blanket 2 further includes a volume-control unit, therein designated 30, enabling the user to conveniently control, from the blanket itself, the sounds produced by the sound transducers 4.

The electrical signals applied to the sound transducers 4 for producing the sounds are generated in sound generator 32. Sound generator 32 is controlled by power switch 34, and by a timer 36 which may be preset to fix the period of operation of the apparatus. A Reset switch 38 may also be included, preferably in the blanket unit 2, to enable the user to conveniently reset the operation time of the apparatus.

FIG. 6 illustrates one implementation of the circuitry included in the block diagram of FIG. 5.

The system illustrated in FIG. 6 comprises a variable-frequency oscillator 40 controlled by a programmable counter-timer 42 for producing a sequence of pleasant tones of a predetermined pitch. Resistors $R_1$–$R_6$ and capacitor $C_1$, set the frequency or the pitch of the output tone sequence, whereas the repetition rate or frequency of the output tones are preset by multivibrator 44, 46 and variable resistor $R_0$. Timer 36 presets the time interval of operation of the system, and may be rest by switch 38. In addition, the output of the tone generator 40 may be attenuated by variable resistor $R_A$ to cause the sounds produced by the transducers 4 to fade out. Resistor $R_A$ is pre-adjustable so as to enable the fade-out to be set at a preselected rate.

FIG. 6 actually illustrates a known form of electronic music synthesizer, and therefore further features of its construction and operation are not set forth. It will be appreciated that other music synthesizers, or other forms of sound generators, could be used for this purpose.

While the invention has been described with respect to two preferred embodiments, it will be appreciated that many other variations, modifications and applications of the invention may be made.

What is claimed is:

1. Apparatus for promoting sleep in an individual, comprising: an article having a relatively large surface area adapted to be placed against and/or around the individual; a plurality of compressional-wave transducers incorporated in said article and distributed over said relatively large surface area at a plurality of different locations thereof for producing compressional waves at said plurality of locations; and electrical circuit means for generating electrical signals energizing said transducers to produce sleep-promoting compressional wave at said plurality of different locations.

2. The apparatus according to claim 1, wherein the article incorporates at least nine of said transducers distributed at different locations thereof.

3. The apparatus according to claim 1, wherein the article is a blanket having inner and outer layers, and said plurality of transducers are sandwiched between said inner and outer layers.

4. The apparatus according to claim 1, wherein said electrical circuit means comprises a signal generator generating monotonous sounds in substantially one persistent tone.

5. The apparatus according to claim 4, wherein said signal generator generates an electrical signal simulating the human heartbeat, said apparatus being particularly useful for promoting sleep in an infant.

6. The apparatus according to claim 5, wherein said electrical circuit means further includes a sound sensor for sensing the crying of the infant and effective, in response thereto, to actuate said signal generator.

7. The apparatus according to claim 5, wherein said electrical circuit means further includes means for presetting the frequency of the signals generated by said signal generator within a range of 40-120 heartbeats per minute.

8. The apparatus according to claim 1, wherein said electrical circuit means generates periodic sounds at a preselected repetition rate and includes means for preselecting said repetition rate.

9. The apparatus according to claim 8, wherein said electrical circuit means includes a variable-frequency oscillator controlled by a programmable counter-timer for producing a sequence of tones of a predetermined pitch.

10. The apparatus according to claim 8, wherein said electrical circuit means further includes preadjustable attenuator means for causing said periodic sounds to fade out at a preselected rate.

11. The apparatus according to claim 1, wherein said electrical circuit means further includes a timer for presetting the period of operation of sound transducers.

12. The apparatus according to claim 1, wherein said electrical circuit means further includes means for varying the amplitude of the compressional waves generated by said electrical circuit.

13. Apparatus for promoting sleep in an individual, comprising: a blanket of relatively large surface are and having inner and outer layers; a plurality of compressional-wave transducers sandwiched between said inner and outer layers at a plurality of different locations for producing compressional waves at said plurality of locations; and means for energizing said transducers to produce sleeppromoting compressional waves at said plurality of different locations.

14. The apparatus according to claim 13, wherein the blanket incorporates at least nine of said transducers distributed at different locations thereof.

15. The apparatus according to claim 13, wherein said means comprises a signal generator generating monotonous sounds in substantially one persistent tone.

16. The apparatus according to claim 15, wherein said signal generator generates an electrical signal simulating the human heartbeat, said apparatus being particularly useful for promoting sleep in an infant.

17. Apparatus for promoting sleep in an individual, comprising: an article of relatively large surface area adapted to be placed against and/or around the individual; a plurality of compressional-wave transducers incorporated in said article and distributed over said relatively large surface area at a plurality of different locations thereof for producing compressional waves at said plurality of locations; and signal generator means for generating electrical signals energizing said transducers to produce sleep-promoting compressional waves simulating the human heartbeat at said plurality of different locations.

18. The apparatus according to claim 17, wherein the article incorporates at least nine of said transducers distributed at different locations thereof.

19. The apparatus according to claim 17, wherein the article is a blanket having inner and outer layers, and said plurality of transducers are sandwiched between said inner and outer layers.

20. The apparatus according to claim 17, wherein said article is adapted to be placed against or around an infant, and said apparatus further includes a sound sensor for sensing the crying of the infant and effective, in response thereto, to actuate said signal generator means.

* * * * *

UNITED STATES PATENT AND TRADEMARK OFFICE
CERTIFICATE OF CORRECTION

PATENT NO. : 4,969,867
DATED : November 13, 1990
INVENTOR(S) : Ruben Cohen

It is certified that error appears in the above-identified patent and that said Letters Patent is hereby corrected as shown below:

Column 3  Line 8, "blanked" should be --blanket--.

Column 3  Line 25, "sounds" should be --sound--.

Column 4  Line 2, "adjust" should be --adults--.

Column 4  Line 30, "rest" should be --reset--.

Column 5  Line 35, "are" should be --area--.

Signed and Sealed this

Fifteenth Day of February, 1994

Attest:

BRUCE LEHMAN

Attesting Officer

Commissioner of Patents and Trademarks